United States Patent
Hammerland, III et al.

(10) Patent No.: US 11,331,144 B2
(45) Date of Patent: May 17, 2022

(54) LIGHT ENERGY SURGICAL SYSTEM, APPARATUS, AND METHOD

(71) Applicant: COVIDIEN LP, Mansfield, MA (US)

(72) Inventors: John A. Hammerland, III, Arvada, CO (US); William H. Nau, Jr., Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 106 days.

(21) Appl. No.: 16/391,502

(22) Filed: Apr. 23, 2019

(65) Prior Publication Data

US 2019/0336218 A1     Nov. 7, 2019

Related U.S. Application Data

(60) Provisional application No. 62/667,168, filed on May 4, 2018.

(51) Int. Cl.
*A61B 18/22*     (2006.01)
*A61B 18/20*     (2006.01)
*A61B 18/00*     (2006.01)

(52) U.S. Cl.
CPC ...... *A61B 18/22* (2013.01); *A61B 2018/0063* (2013.01); *A61B 2018/00601* (2013.01); *A61B 2018/205545* (2017.05); *A61B 2018/2266* (2013.01)

(58) Field of Classification Search
CPC ........ A61B 18/22; A61B 2018/205545; A61B 2018/00601; A61B 2018/0063; A61B 2018/2266
See application file for complete search history.

(56) References Cited

U.S. PATENT DOCUMENTS

| | | | |
|---|---|---|---|
| 4,985,030 A | 1/1991 | Melzer et al. | |
| 5,532,771 A * | 7/1996 | Johnson | A61B 5/1171 351/211 |
| 6,387,043 B1 * | 5/2002 | Yoon | A61B 1/00052 600/104 |
| 6,419,626 B1 * | 7/2002 | Yoon | A61B 1/00052 600/103 |
| 7,387,126 B2 | 6/2008 | Cox et al. | |
| 8,083,739 B2 | 12/2011 | Messerly | |
| 8,876,811 B2 * | 11/2014 | Lewinsky | A61B 18/22 606/16 |

(Continued)

FOREIGN PATENT DOCUMENTS

EP     0706780     4/1996

*Primary Examiner* — Christopher A Flory
(74) *Attorney, Agent, or Firm* — Carter, DeLuca & Farrell LLP

(57) ABSTRACT

A surgical instrument includes a light guide configured to convey light energy, a lens configured to focus the light energy into a light beam, a mounting tube, a jaw assembly coupled to the mounting tube, and a handle assembly. The jaw assembly includes a first jaw member non-movably secured to the mounting tube, a second jaw member movably secured to the mounting tube, and a window secured to the first jaw member and forming a tissue contacting surface. The window is oriented in a plane oblique to a longitudinal axis of the mounting tube and forms a liquid-tight seal between tissue and the lens. The handle assembly is coupled to the jaw assembly to move the second jaw member between an open position in which the second jaw member is spaced part from the window and a closed position.

20 Claims, 6 Drawing Sheets

(56) References Cited

U.S. PATENT DOCUMENTS

| | | | |
|---|---|---|---|
| 9,113,934 B2 | 8/2015 | Chernov et al. | |
| 9,241,728 B2* | 1/2016 | Price | A61B 18/1445 |
| 9,375,282 B2 | 6/2016 | Nau, Jr. et al. | |
| 9,610,121 B2* | 4/2017 | Nau, Jr. | A61B 18/28 |
| 10,842,588 B2* | 11/2020 | Hansen | A61B 34/30 |
| 2008/0051773 A1* | 2/2008 | Ivanov | A61N 5/0616 |
| | | | 606/12 |
| 2008/0097519 A1* | 4/2008 | Calderon | A61B 17/0401 |
| | | | 606/205 |
| 2011/0082449 A1* | 4/2011 | Melsky | A61B 18/24 |
| | | | 606/14 |
| 2012/0046660 A1* | 2/2012 | Nau, Jr. | A61B 17/32002 |
| | | | 606/45 |
| 2012/0316549 A1* | 12/2012 | Lewinsky | A61N 5/0603 |
| | | | 606/16 |
| 2013/0253489 A1* | 9/2013 | Nau, Jr. | A61B 17/29 |
| | | | 606/16 |
| 2014/0107443 A1* | 4/2014 | Hoarau | A61B 18/1233 |
| | | | 600/342 |
| 2014/0213848 A1* | 7/2014 | Moskowitz | A61B 1/018 |
| | | | 600/106 |
| 2014/0336456 A1* | 11/2014 | Demers | A61B 10/04 |
| | | | 600/106 |
| 2014/0364875 A1* | 12/2014 | Zentgraf | A61B 17/29 |
| | | | 606/144 |
| 2016/0302860 A1* | 10/2016 | Nau, Jr. | A61B 18/18 |
| 2016/0346034 A1* | 12/2016 | Arya | A61B 18/1445 |
| 2016/0347237 A1* | 12/2016 | Bhakta | F21S 41/285 |
| 2019/0201136 A1* | 7/2019 | Shelton, IV | A61B 17/0206 |
| 2019/0206562 A1* | 7/2019 | Shelton, IV | A61B 1/00011 |
| 2020/0138430 A1* | 5/2020 | Zentgraf | A61B 17/0482 |

* cited by examiner

LIGHT ENERGY SURGICAL SYSTEM, APPARATUS, AND METHOD

CROSS REFERENCE TO RELATED APPLICATION

The present application claims the benefit of and priority to U.S. Provisional Application Ser. No. 62/667,168, filed on May 4, 2018 the entire contents of which are incorporated herein by reference.

BACKGROUND

1. Technical Field

The present disclosure generally relates to light energy surgical devices. More particularly, the present disclosure relates to systems, apparatuses, and methods for applying light energy for treatment of tissue.

2. Background of Related Art

Light energy surgical systems are used in surgical procedures to treat the tissue of a patient using light energy. Such a system can be used for cutting or sealing the tissue of a patient with light energy. During operation, light energy from a generator is guided to an instrument that grasps tissue, and the light energy is used to treat tissue grasped by the instrument.

In comparison to electrosurgical instruments, which apply electrical energy to treat tissue, light energy surgical instruments are simpler in that they generally require fewer components at the tissue contacting portion. Unlike electrosurgical instruments, a light energy surgical instrument generally does not require electrical wiring and insulation at the tissue contacting portion, nor components such as sealing plates.

Accordingly, in view of the benefits of light energy surgical technology, there is continuing interest in development and improvement of light energy surgical instruments, systems, and methods.

SUMMARY

The present disclosure relates to systems, apparatuses, and methods for applying light energy for treatment of tissue. As will be described herein in more detail, a light energy surgical instrument in accordance with the present disclosure includes a jaw having an angled jaw member and tissue contacting window for grasping tissue to be treated by light energy.

In accordance with aspects of the present disclosure, a surgical instrument includes a mounting tube defining a longitudinal axis and having a proximal portion and a distal portion, a light guide disposed inside the mounting tube and configured to convey light energy, at least one lens positioned distal to the light guide and configured to focus the light energy into a light beam, a jaw assembly coupled to the distal portion of the mounting tube and positioned distal to the at least one lens, and a handle assembly. The jaw assembly includes a first jaw member non-movably secured to the distal portion of the mounting tube, a second jaw member movably secured to the distal portion of the mounting tube, and a window secured to the first jaw member and forming a tissue contacting surface. The window is oriented in a plane oblique to the longitudinal axis and forms a liquid-tight seal between tissue and the at least one lens. The handle assembly is coupled to the jaw assembly and is operable to move the second jaw member between an open position in which the second jaw member is spaced part from the window and a closed position. In various embodiments, the handle assembly is movable to cause the jaw assembly to exert different pressures on tissue grasped by the jaw assembly.

In various embodiments, the second jaw member includes a tissue contacting surface that includes a light-reflective material. In various embodiments, the surgical instrument includes a blast shield coupled to the light guide, where the blast shield blocks reflected light from reaching the source of the light energy. In various embodiments, the second jaw member includes a tissue contacting surface that includes a light-absorbent material.

In various embodiments, the at least one lens is inside the mounting tube and includes a collimator, a beam-shaping lens distal to the collimator, and a focusing lens distal to the beam-shaping lens. In various embodiments, the beam-shaping lens outputs the light beam substantially in the shape of a line. In various embodiments, the beam-shaping lens outputs the light beam substantially in the shape of a rectangle or an oval.

In accordance with aspects of the present disclosure, a surgical system includes a light energy generator configured to provide light energy and a surgical instrument coupled to the light energy generator. The surgical instrument can include the embodiments described above herein.

In accordance with aspects of the present disclosure, a surgical method includes moving a jaw assembly between an open position and a closed position to grasp tissue, where the jaw assembly includes a first jaw member non-movably secured to a distal portion of a mounting tube, a second jaw member movably secured to the distal portion of the mounting tube, and a window secured to the first jaw member. The window forms a tissue contacting surface and is oriented in a plane oblique to a longitudinal axis of the mounting tube. When the jaw assembly is in the open position, the second jaw member is spaced part from the window. The method further includes conveying light energy through a light guide disposed inside the mounting tube, to at least one lens positioned distal to the light guide, focusing the light energy into a light beam using the at least one lens, and applying the light beam through the window to the tissue grasped by the jaw assembly. The window forms a liquid-tight seal between the tissue and the at least one lens. In various embodiments, the method includes exerting different pressures on the tissue grasped by the jaw assembly.

In various embodiments, the method includes reflecting at least a portion of the light beam from a tissue contacting surface of the second jaw member, where the tissue contacting surface of the second jaw member includes a light-reflective material. In various embodiments, the method includes blocking reflected light from reaching a source of the light energy using a blast shield coupled to the light guide. In various embodiments, the method includes absorbing at least a portion of the light beam at a tissue contacting surface of the second jaw member, where the tissue contacting surface of the second jaw member includes a light-absorbent material.

In various embodiments, focusing the light energy into a light beam using the at least one lens includes collimating the light energy into collimated light energy, shaping the collimated light energy into a shaped light energy, and focusing the shaped light energy into the light beam. In various embodiments, the shaped light energy has the shape of a line. In various embodiments, the shaped light energy has the shape of a rectangle or an oval.

Further details and aspects of exemplary embodiments of the present disclosure are described in more detail below with reference to the appended figures.

BRIEF DESCRIPTION OF THE DRAWINGS

Various embodiments of the present disclosure are described with reference to the accompanying drawings wherein.

DETAILED DESCRIPTION

The present disclosure relates to systems, apparatuses, and methods for applying light energy for treatment of tissue. As will be described herein in more detail, a light energy surgical instrument in accordance with the present disclosure includes a jaw having an angled jaw member and tissue contacting window for grasping tissue to be treated by light energy.

Light (e.g., from about 200 nm to about 11,000 nm) can be used to heat tissue due to absorption of light. Absorption, transmittance, and scattering of light energy depends on the tissue, the state of the tissue (e.g., hydration, disease state, treatment stage, etc.), and the wavelength of the light. Controlling the distribution of energy within the tissue based on an appropriate choice of wavelength is disclosed in U.S. Pat. No. 9,375,282, which is hereby incorporated by reference herein in its entirety. More specifically, wavelengths that are strongly absorbed by the tissue deposit energy closer to the surface of the tissue while wavelengths that are weakly absorbed by the tissue are used to deposit a larger fraction of the incident energy deeper in the tissue. In particular, since tissue is relatively transparent to light at certain infrared wavelengths, light energy at infrared frequencies may be used for deeper energy deposition.

Figure 1:
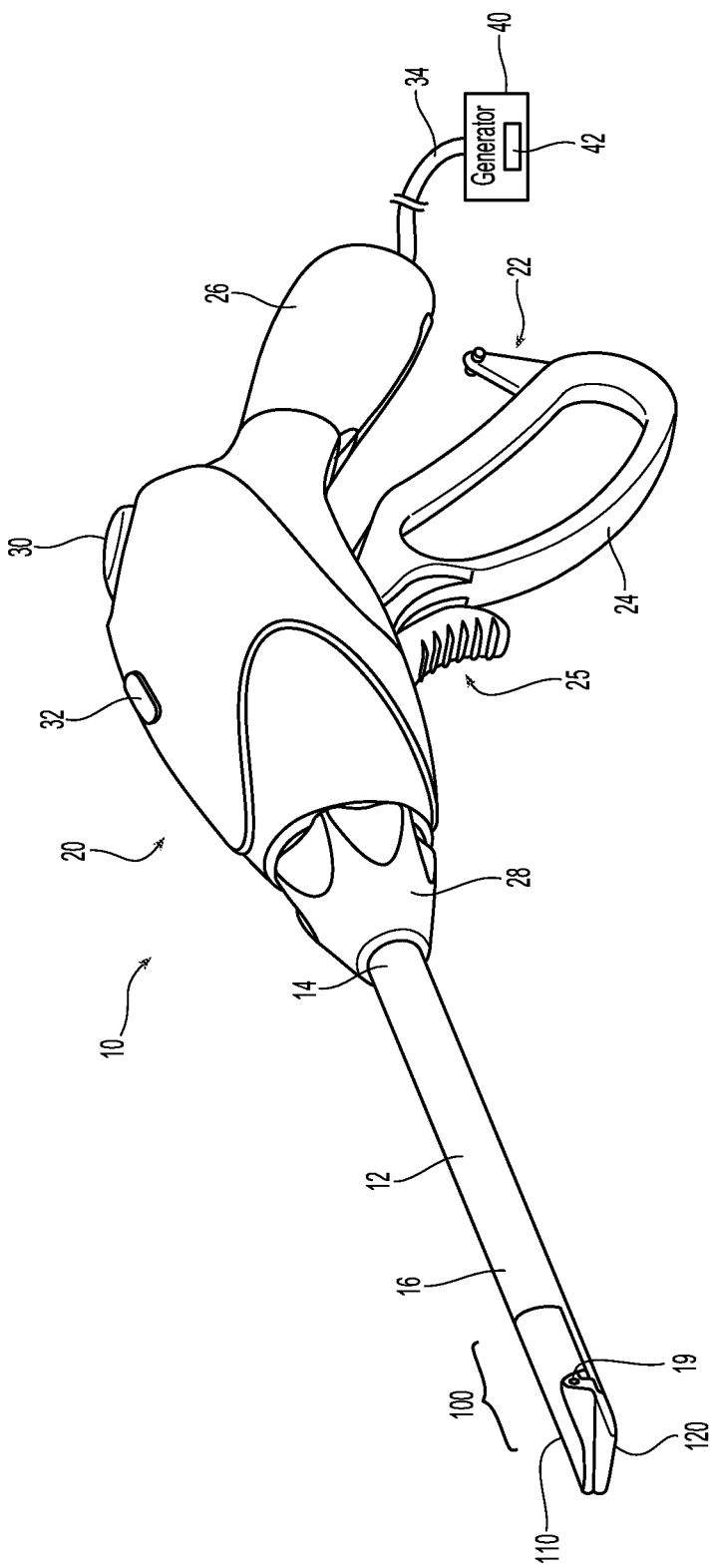
FIG. 1 is a diagram of an exemplary light energy system, in accordance with aspects of the present disclosure.

Referring now to FIG. 1, an exemplary embodiment of a light energy instrument 10 is coupled to a generator 40 for generating light energy adapted to treat tissue. Generator 40 is configured to output various types of energy, such as light energy having a wavelength from about 200 nm to about 11,000 nm. In various embodiments, the light source within the generator 40 can be a laser diode or another type of light source. The instrument 10 is coupled to the generator 40 via a cable 34 that is adapted to transmit light energy and control signals therebetween. Various embodiments of the instrument 10 utilizing the aforementioned light energy are discussed in more detail below.

The instrument 10 includes a jaw assembly 100, a housing 20, a handle assembly 22, a trigger assembly 25, and a rotating assembly 28. These components enable the instrument 10 and the jaw assembly 100 to cooperate to grasp, seal, and/or divide tissue. In the illustrated embodiment, the handle assembly 22 includes a fixed handle 26 that is integral with housing 20 and a moveable handle 24. The moveable handle 24 is moveable relative to the fixed handle 26 and is coupled to the jaw assembly 100 via a drive assembly (not shown). Various types of drive assemblies are known to persons skilled in the art.

In various embodiments, the trigger assembly 25 may be configured to activate the delivery of light energy. The instrument 10 also includes a shaft 12 having a distal portion 16 that supports the jaw assembly 100, and a proximal portion 14 that mechanically engages the housing 20 and the rotating assembly 28. The rotating assembly 28 is mechanically engaged with the shaft 12 such that rotational movement of the rotating assembly 28 imparts corresponding rotational movement to the shaft 12, which, in turn, rotates the jaw assembly 100. In various embodiments, the rotating assembly 28, the shaft 12, and the jaw assembly 100 can be mechanically coupled such that they have unlimited rotation.

The jaw assembly 100 includes two jaw members 110, 120. One jaw member 110 is fixed and non-moveable, and the other jaw member 120 is pivotable about a pin 19. The movable jaw member is movable between an open position in which jaw members 110, 120 are spaced relative to another, and a closed position, which will be described in more detailed later herein. In accordance with aspects of the present disclosure, movement of the jaw members 110, 120 is coupled to movement of the moveable handle 24, such that the handle assembly 22 is used to open and close the jaw assembly 100. In various embodiments, movement of the handle 24 permits the jaw assembly 100 to exert varying amounts of pressure to tissue grasped by the jaw assembly 100. In various embodiments, exerting a sufficient amount of pressure to the tissue, in combination with treating the tissue with light energy, can cause the tissue to divide, even when the pressure alone or the light energy alone is insufficient to cause the tissue to divide. The positions of movable and non-movable jaw members are exemplary. In various embodiments, jaw member 110 may be moveable and jaw member 120 may be non-moveable. In various embodiments, both jaw members 110, 120 may be movable.

First and second switch assemblies 30 and 32 are configured to selectively provide light energy to the jaw assembly 100. More particularly, the first switch assembly 30 may be associated with a first type of surgical procedure (e.g., vessel sealing) and the second switch assembly 32 may be associated with a second type of surgical procedure (e.g., vessel cutting). The switch assemblies 30, 32 are exemplary, and other suitable switch assemblies are contemplated to be within the scope of the present disclosure. Further, the presently disclosed embodiments may be configured to perform various types of surgical procedures other than sealing and cutting.

Handle assembly 22 further includes one or more-light transmissive elements, such as a cable 34 that connects the instrument 10 to the generator 40. The cable 34 may include one or more optical fibers to transmit light energy through various paths and ultimately to the jaw assembly 100.

Figure 2:
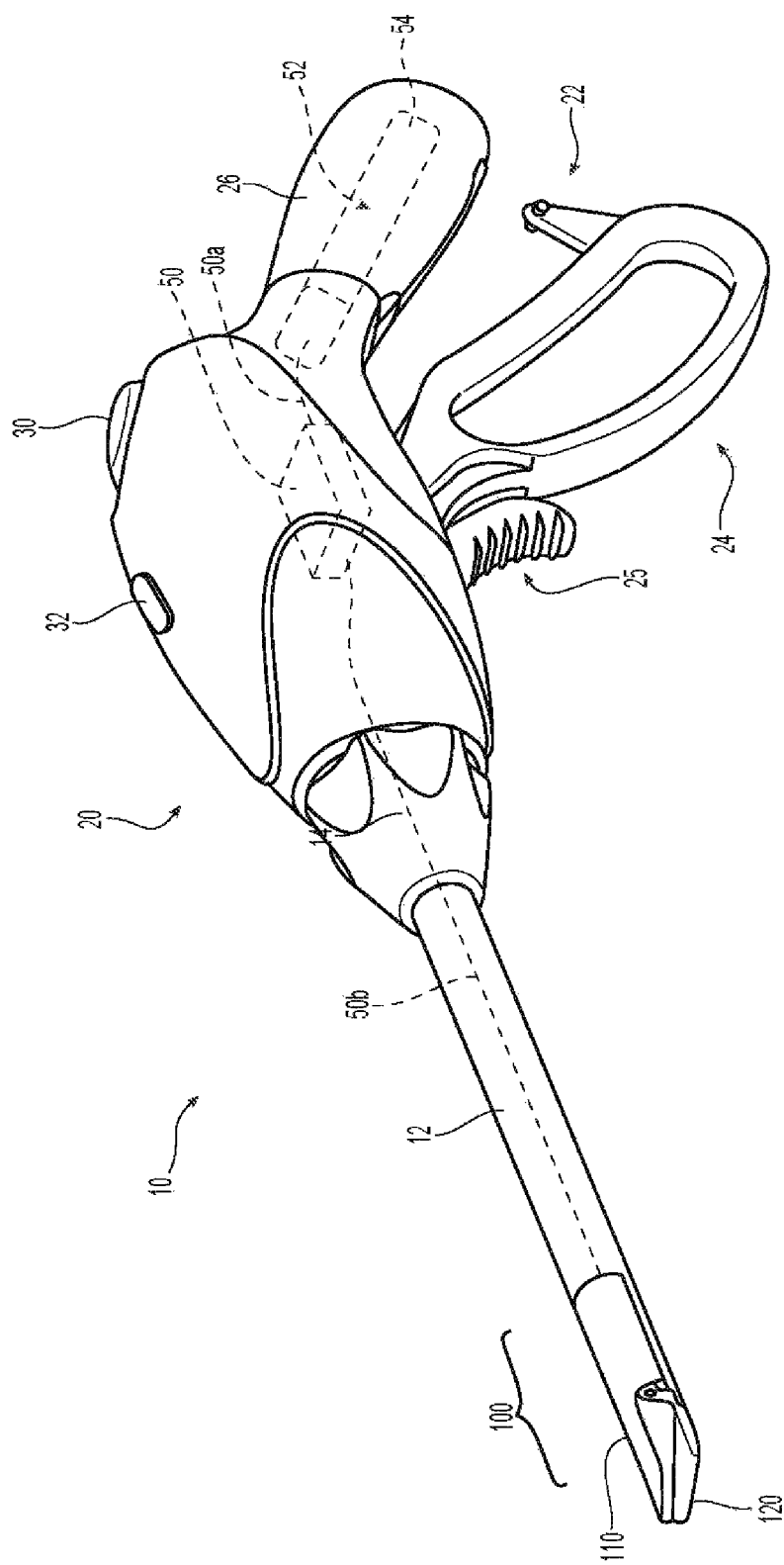
FIG. 2 a diagram of an exemplary light energy instrument, in accordance with aspects of the present disclosure with an internal energy source shown in phantom.

Referring now to FIG. 2, another embodiment of a light energy surgical instrument 10 is shown, which includes an internal energy source 50 for generating light energy that is operably coupled to a battery compartment 52 via one or more wires 50a. In various embodiments, one or more battery operated laser diodes or fiber lasers may also be used to provide a portable light energy source. The internal energy source 50 may be configured to provide light energy to the jaw assembly 100 via one or more laser fibers 50b or via another suitable transmission medium. The battery compartment 52 may be configured to receive one or more batteries 54 for providing energy to the internal energy source 50. The battery compartment 52 may be defined within a suitable portion of the housing 20 of the instrument 10, such as within the fixed handle 26, as shown in FIG. 2. In various embodiments, a controller (not shown) may also be disposed within the instrument 10 (e.g., within the housing).

Figure 3:
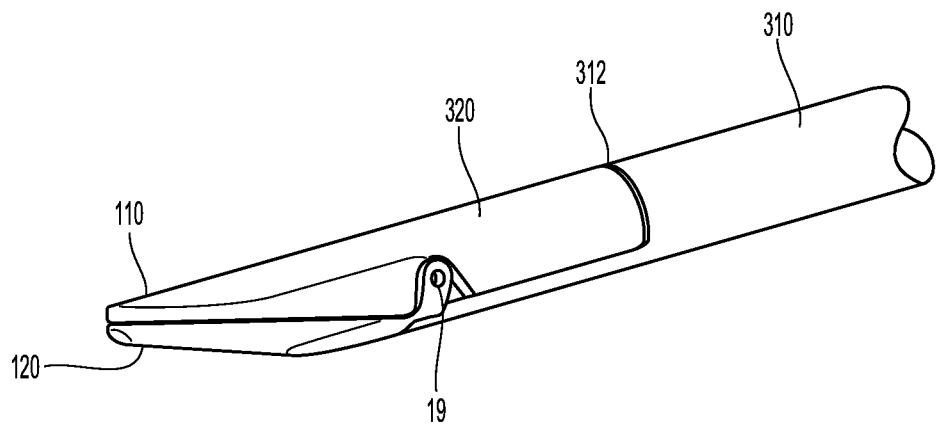
FIG. 3 is an enlarged diagram of an exemplary distal portion of a light energy instrument, in accordance with aspects of the present disclosure.

FIG. 3 shows an embodiment of the distal portion of a light energy surgical instrument, including a distal portion of a shaft 310, a distal portion of a mounting tube 320, and a jaw assembly 100. In the illustrated embodiment, the shaft 310 and the mounting tube 320 are both cylindrical, and the mounting tube 320 is positioned radially within the shaft 310. A portion of the mounting tube 320 extends axially beyond an upper end 312 of the shaft 310, and a lower portion of the shaft 310 extends axially beyond a lower end of the mounting tube 320.

The jaw assembly 100 includes an upper jaw member 110 and a lower jaw member 120. In the illustrated embodiment, the upper jaw member 110 is integral with the mounting tube 320. In various embodiments, the upper jaw member 110 need not be integrated with the mounting tube 320 and can be non-movably secured to the mounting tube 320 by, for example, soldering or fasteners. The upper jaw member 110 includes an outer surface portion that is aligned with an outer surface portion of the mounting tube 320. The lower jaw member 120 is secured to the mounting tube by a pin 19, which allows the lower jaw member 120 to pivot relative to the mounting tube 320. Movement of the lower jaw member 120 is actuated by the handle assembly 22 described in connection with FIG. 1, through a drive assembly which persons skilled in the art will understand.

In accordance with an aspect of the present disclosure, the jaw assembly 100 includes a closed position, which is illustrated in FIG. 3. In the closed position, the upper jaw member 110 and the lower jaw member 120 contact each other at a plane of contact that is oblique to a longitudinal axis of the shaft 310 and mounting tube 320. As used herein, and as commonly understood, the term "oblique" means neither parallel nor perpendicular. Accordingly, as shown in FIG. 3, the plane of contact between the upper jaw member 110 and the lower jaw member 120 is configured to form an angle relative to the longitudinal axis of the shaft/mounting tube and is neither parallel to the longitudinal axis nor perpendicular to the longitudinal axis. In various embodiments, the jaw assembly 100 can be modified for different types of surgical procedures, and the angle of the contact plane between the upper and lower jaw members 110, 120 can also vary depending on the size and dimensions of the jaw assembly 100. In various embodiments, the upper and lower jaw members may not contact each other in the closed position. Rather, a hard stop in the jaw assembly can bring the jaw members to a close but spaced-part orientation, such as parallel orientation, without touching.

The embodiment illustrated in FIG. 3 is exemplary and variations are contemplated to be within the scope of the present disclosure. For example, the shaft 310 and/or the mounting tube 320 can have shapes, geometries, and dimensions different from those illustrated. In various embodiments, the lower jaw member can be non-movably secured to the mounting tube 320 or the shaft 310, while the upper jaw member can be movably secured to the mounting tube 320 or the shaft 310. In various embodiments, one or both of the upper and lower jaw members can be secured to the shaft rather than to the mounting tube. In various embodiments, both the upper and lower jaw members can be movable.

Figure 4:
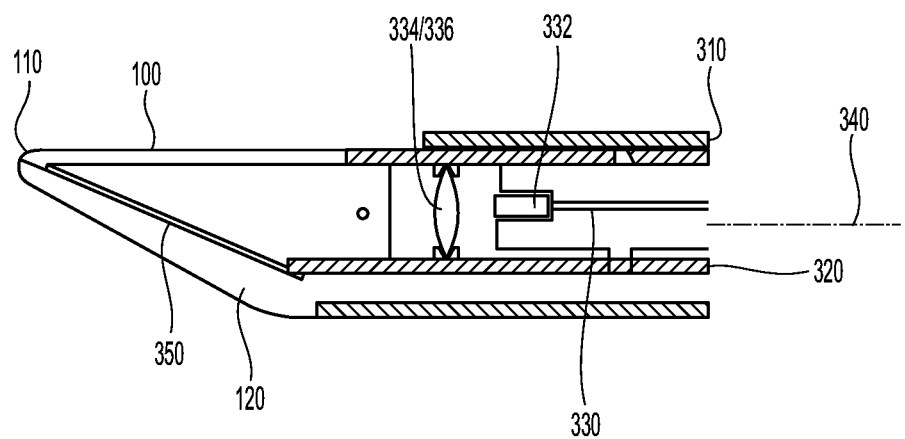
FIG. 4 is a cross-sectional diagram showing exemplary components of a light energy instrument, in accordance with aspects of the present disclosure.

Referring now to FIG. 4, there is shown a cross-sectional view of various exemplary components in the distal portion of a light energy instrument, including a shaft 310, a mounting tube 320, a jaw assembly 100, and an optical assembly 330-336. As used herein, the term "optical assembly" refers to components that operate with light in the range of 200 nm through 11,000 nm, or that operate with light within a subset of this range of wavelengths. Accordingly, the disclosed optical assembly is not limited to operating only with visible light.

The optical assembly includes a light guide 330, such as optical fiber, and one or more lenses, such as a collimating lens 332, a light beam-shaping lens 334, and a focusing lens 336. The light guide 330 is disposed within the shaft 310 and the mounting tube 320. The light guide 330 connects to a light energy generator (e.g., FIG. 1, 40) and conveys light energy produced by the generator. In various embodiments, the light guide 330 may or may not be parallel or substantially parallel to the longitudinal axis 340 of the shaft and mounting tube. As described above in connection with FIG. 1, the shaft 310, the mounting tube 320, and the jaw assembly 100 can have unlimited rotation. In various embodiments, a distal portion of the light guide 330 can rotate with the mounting tube 320, and a proximal portion of the light guide 330 can remain fixed such that it does not rotate with the mounting tube 320. In various embodiments, the rotating and non-rotating portions of the light guide 330 can be coupled to each other by an optical coupler (not shown) that couples light energy between the two portions while permitting one portion to rotate relative to the other portion. Persons skilled in the art will recognize such an optical coupler. In various embodiments, all or a portion of the light guide 330 can twist as long as its distal end remains in a fixed orientation relative to the lenses, such as the collimating lens 332, the light beam-shaping lens 334, and/or the focusing lens 336.

Figure 5:
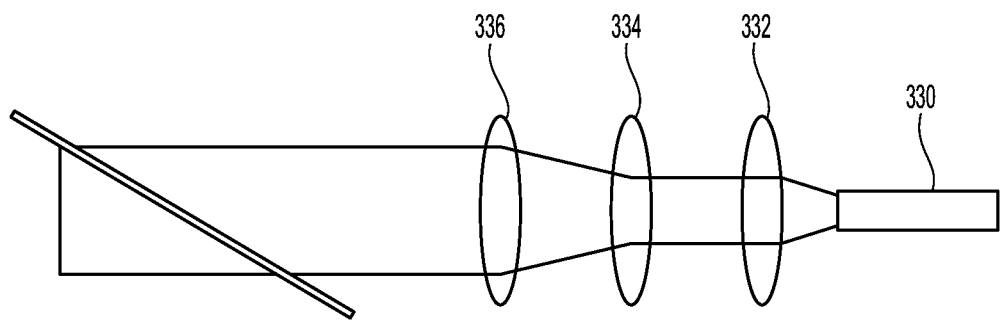
FIG. 5 is a schematic diagram of an exemplary path of a light beam through a light energy instrument, in accordance with aspects of the present disclosure.

With reference also to FIG. 5, light exiting the light guide 330 is directed to the collimating lens 332, which produces parallel light beams at its output. The parallel light beams are directed to the beam-shaping lens 334, which shapes the parallel light beams into a particular cross-sectional shape. Then, a focusing lens 336 focuses the shaped light beam onto the jaw assembly 100. In various embodiments, the beam-shaping lens 334 can produce a light beam at its output in the shape of a line; that is, the cross section of the light beam is a line or is substantially a line. In various embodiments, the beam-shaping lens 334 can produce a light beam at its output in the shape of a rectangle; that is, the cross section of the light beam is a rectangle or is substantially a rectangle. In various embodiments, the beam-shaping lens 334 can produce a light beam at its output in the shape of an oval; that is, the cross section of the light beam is an oval or is substantially an oval. The light beam may not be exactly a particular shape, but rather may be substantially a particular shape because of factors such as imperfections in a lens or beam degradation at the periphery of the beam profile, among other factors.

In accordance with aspects of the present disclosure, a light beam in the shape of a line may be advantageous for a vessel cutting operation, whereas a light beam in the shape of a rectangle or oval may be advantageous for a vessel sealing operation. Other light beam shapes are contemplated to be within the scope of the present disclosure, including, for example, a triangle shaped light beam or a light beam in the shape of another polygon; that is, the cross section of the light beam is in the shape of a polygon. In various embodiments, the light beam output by an optical assembly 330-336 can be parallel or substantially parallel to the longitudinal axis 340 of the shaft and mounting tube. In various embodiments, the light beam output by an optical assembly 330-336 can be oblique to the longitudinal axis 340.

In various embodiments, the light energy instrument can include multiple optical assemblies. Accordingly, multiple light guides and multiple sets of lenses can be disposed within the shaft and the mounting tube. For example, two or more light guides 330 may be vertically or adjacently stacked, and two or more sets of corresponding lenses 332-336 may be vertically or adjacently stacked. In embodiments having multiple optical assemblies, an optical assembly may provide a light beam that is parallel to the longitudinal axis, and another optical assembly may provide a light beam that is non-parallel to the longitudinal axis. In various embodiments, the light beams produced from different optical assemblies may be directed in different directions. Additionally, in embodiments having multiple optical assemblies, an optical assembly may provide a light beam in the shape of a line, and another optical assembly may provide a light beam in the shape of a polygon, such as a rectangle, or in the shape of an oval. As mentioned above, a light beam in the shape of a line may be advantageous for a vessel cutting operation, whereas a light beam in the shape of a rectangle or oval may be advantageous for a vessel sealing operation. The different optical assemblies can be coupled to the switches (FIG. 1, reference numbers 30, 32) on the instrument, which select either a vessel sealing mode or a vessel cutting mode. Depending on the selected mode, a particular optical assembly could be activated to produce the light beam shape that is associated with the selected mode.

In various embodiments, and with reference to FIG. 4 and FIG. 5, the light beam-shaping lens 334 can be rotatable and can include multiple sub-lenses (not shown) that provide different beam shapes. As the light beam-shaping lens 334 rotates, a different sub-lens can be positioned in the path of the light beam. In various embodiments, one sub-lens can provide a light beam in the shape of a line, and another sub-lens can provide a light beam in the shape of a polygon, such as a rectangle, or in the shape of an oval. In various embodiments, the sub-lenses can be housed within a rotating housing.

In various embodiments, the light energy instrument may not include any lenses. Rather, the optical assembly can include a light guide whose distal end is shaped to provide a particular beam shape, such that no light-beam shaping lens is needed. In various embodiments, such an optical assembly may include a focusing lens but may not include a collimating lens. In various embodiments, such an optical assembly may not include either a focusing lens or a collimating lens.

With continuing reference to FIG. 4, the light beam output by the optical assembly 330-336 is directed toward the jaw assembly 100. In accordance with aspects of the present disclosure, the light beam is directed through a window 350 that is secured to the upper jaw member 110 and that forms a tissue contacting surface. In various embodiments, the window 350 can be a sapphire crystal window. In various embodiments, the window 350 can be made from another material, such as a material formulated to deliver dramatically improved damage resistance while allowing improved in-field performance, commonly sold under the tradename Gorilla glass by Corning Incorporated. In various embodiments, the window 350 is oriented in a plane that is oblique to the longitudinal axis 340 of the shaft 310 or mounting tube 320. When the jaw assembly 100 is in the closed position, the lower jaw member 120 contacts the upper jaw member 110. When the jaw assembly 100 is in the open position, the lower jaw member 120 is spaced apart from and does not contact the window 350. In various embodiments, in the closed position, the second jaw member can contact with the window 350. In various embodiments, in the closed position, the second jaw member may not contact the window 350. In various embodiments, the first and second jaw members may not contact each other in the closed position. Rather, a hard stop in the jaw assembly can bring the jaw members to a close but spaced-part orientation, such as parallel orientation, without touching.

In one aspect of the present disclosure, the window 350 forms a liquid-tight seal between tissue and the optical assembly 330-336. If liquid seeps into the optical assembly 330-336, such liquid could cause undesirable heat buildup. In one embodiment, as shown in FIG. 4, the window 350 connects between a distal portion of the first jaw member 110 and a lower end of the mounting tube 320 so that no liquid is able to enter the cavity of the mounting tube 320. In this manner, when the window 350 acts as a tissue contacting surface and tissue is grasped by the jaw assembly 100, the optical assembly 330-336 within the mounting tube 320 is protected from direct contact with the tissue or any liquid from the tissue. Other embodiments are contemplated for preventing liquid from contacting the optical assembly 330-336. For example, in various embodiments, the optical assembly 330-336 can be encapsulated in a vacuum chamber. In various embodiments, various components of the optical assembly 330-336 can be encapsulated in liquid-free chambers, while liquid may be permitted to enter spaces between the chambers. The described embodiments are merely exemplary and do not limit the scope of the present disclosure.

With continuing reference to FIG. 4, in various embodiments, the lower jaw member 120 has a tissue contacting surface that may include a light-reflective material, which may be, but is not limited to, polished metal or a coating that is adapted to reflect light. Some light may reach the lower jaw member 120 by passing through the tissue grasped by the jaw assembly 100. Reflecting such light from the tissue contacting surface of the lower jaw member 120 will direct such light back to the tissue and enhance the effectiveness of the light energy treatment. However, reflected light may also pass through the tissue and enter the mounting tube 320 through the window 350. If reflected light energy enters the light guide 330 and reaches the generator, it may damage the light energy source, such as a laser diode. In various embodiments, a blast shield (not shown) is coupled to the light guide 330 to block reflected light from reaching the source of the light energy. Persons skilled in the art will recognize a blast shield and will understand its implementation.

In various embodiments, the tissue contacting surface of the lower jaw member 120 can include a light absorbent material, such as a thermochromic material configured to increase light absorption as temperature increases. As used herein, the term "thermochromic" refers to materials that change color in response to a change in temperature. As the temperature of the jaw assembly 100 increases during application of light energy, the thermochromic material becomes progressively more light absorbent and consequently also provides heat to the tissue.

Accordingly, described above are systems and instruments for providing and applying light energy to tissue. The following will describe a corresponding method for applying light energy.

Figure 6:
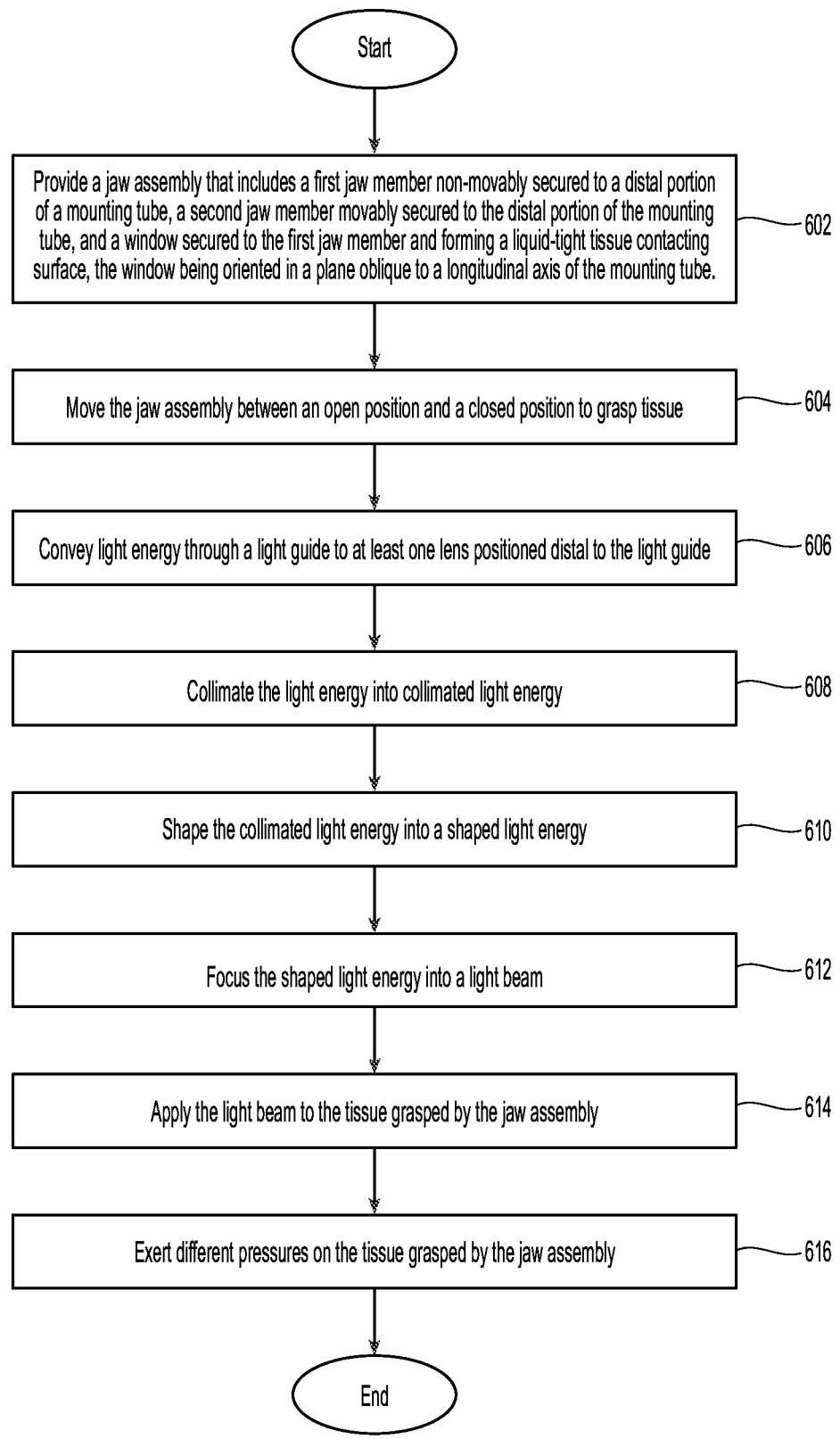
FIG. 6 is a flow chart of an exemplary method of applying light energy, in accordance with aspects of the present disclosure.

Referring to FIG. 6, there is shown a flow chart of an exemplary method of applying light energy. Referring also to FIG. 4, the method provides, at step 602, the jaw assembly 100 described above herein, which includes a first jaw member 110 non-movably secured to the distal portion of the mounting tube 310, a second jaw member 120 movably secured to the distal portion of the mounting tube 320, and a window 350 secured to the first jaw member 110. The window 350 forms a tissue contacting surface and is oriented in a plane oblique to the longitudinal axis 340 of the mounting tube 320. When the jaw assembly 100 is in the open position, the second jaw member 120 is spaced apart from the first jaw member 110 and is not in contact with the window 350. And when the jaw assembly 100 is in the closed position, the second jaw member 120 contacts the first jaw member 110. Additionally, the window 350 forms a liquid-tight seal between the tissue and optical components such as a lens 334/336. In various embodiments, in the closed position, the second jaw member is in contact with the window 350. In various embodiments, the first and second jaw members may not contact each other in the closed position. Rather, a hard stop in the jaw assembly can bring the jaw members to a close but spaced-part orientation, such as parallel orientation, without touching.

At step 604, the method involves moving the jaw assembly 100 between the open position and the closed position to grasp tissue. At step 606, light energy is conveyed through a light guide 330 that is disposed inside a mounting tube 320, to one or more lenses 320-336 positioned distal to the light guide 330. The lenses 332-336 focus the light energy into a light beam in steps 608-612, and the light beam is applied to the tissue grasped by the jaw assembly 100 at step 614. Focusing the light energy into a light beam includes collimating the light energy into collimated light energy in step 608, shaping the collimated light energy into a shaped light energy in step 610, and focusing the shaped light energy into the light beam in step 612. The method can optionally, at step 616, include exerting different pressures on the tissue grasped by the jaw assembly 100. As mentioned above herein, exerting a sufficient amount of pressure to the tissue, in combination with treating the tissue with light energy, can cause the tissue to divide, even when the pressure alone or the light energy alone is insufficient to cause the tissue to divide.

Figure 7:
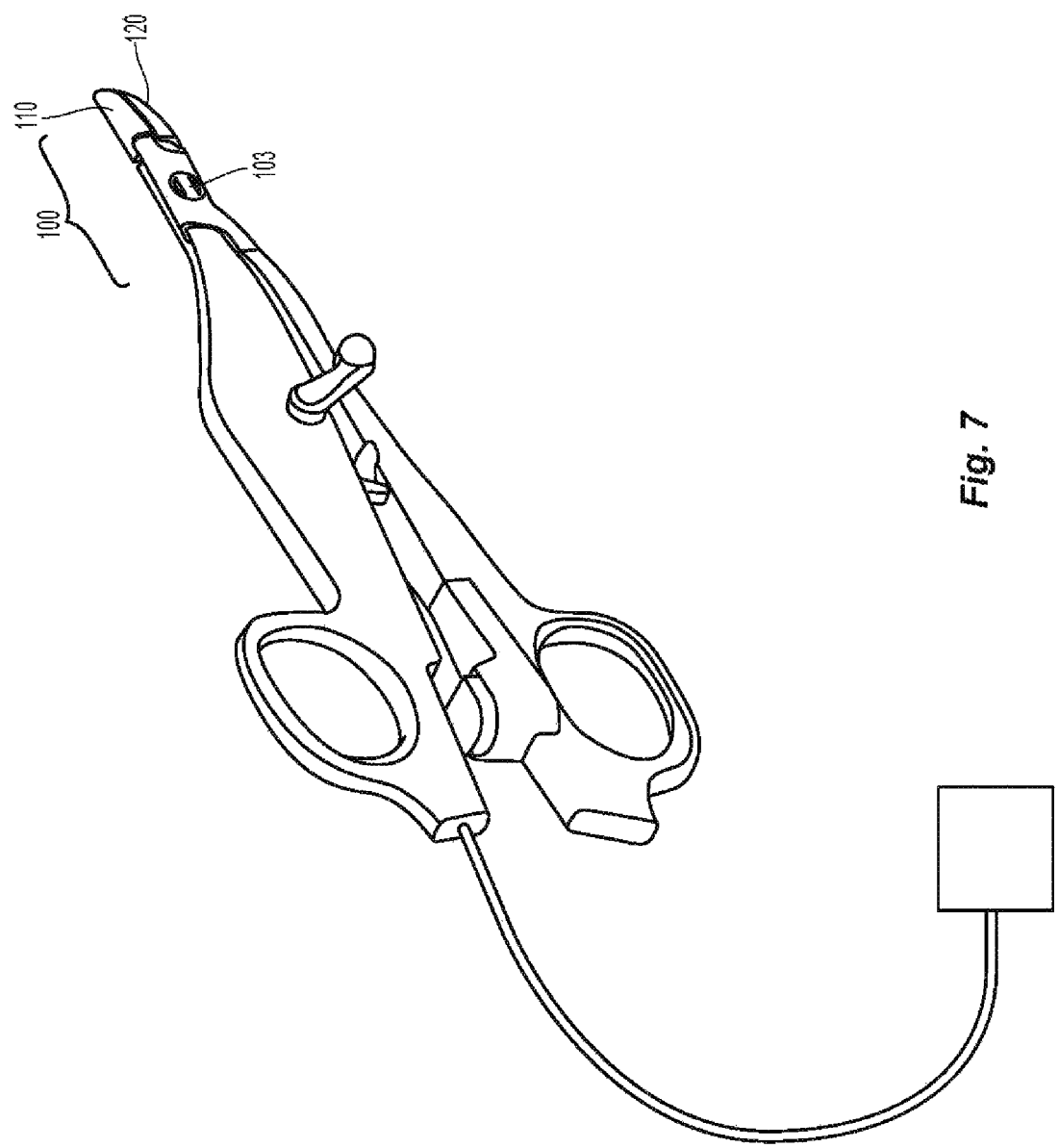
FIG. 7 is a diagram of an exemplary light energy system with hemostat forceps, in accordance with aspects of the present disclosure.

Referring now to FIG. 7, there is shown a light energy system having a hemostat forceps that is coupled to a generator via a cable. The hemostat forceps includes a jaw assembly 100 having two jaw members 110, 120 and a pivot point 103. Aspects of the present disclosure described above herein are applicable to the hemostat forceps and the jaw assembly 100 of the hemostat forceps, including, but not limited to, aspects described and shown in connection with FIG. 4.

Accordingly, described here are systems, apparatuses, and methods, for providing, controlling, and applying light energy. The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

The systems, apparatuses, and methods described herein may also utilize one or more controllers to receive information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

The controller(s) may implement methods, programs, algorithms or codes using a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A surgical instrument, comprising:
    a mounting tube defining a longitudinal axis and having a proximal portion and a distal portion;
    a light guide disposed inside the mounting tube and configured to convey light energy, a distal end of the light guide ending within the mounting tube;
    at least one lens positioned entirely inside the mounting tube and distal to the light guide and configured to focus the light energy to provide a light beam;
    a jaw assembly coupled to the distal portion of the mounting tube and positioned distal to the at least one lens such that the light beam provided by the at least one lens enters the jaw assembly, the jaw assembly including:
        a first jaw member non-movably secured to the distal portion of the mounting tube,
        a second jaw member movably secured to the distal portion of the mounting tube, and
        a window secured to the first jaw member and forming a tissue contacting surface, the window being oriented in a plane oblique to the longitudinal axis and forming a liquid-tight seal between tissue and the at least one lens; and
    a handle assembly coupled to the jaw assembly and operable to move the second jaw member between an open position in which the second jaw member is spaced apart from the window and a closed position.

2. The surgical instrument of claim 1, wherein the second jaw member includes a tissue contacting surface that includes at least one of: a light-reflective material or a light-absorbent material.

3. The surgical instrument of claim 2, further comprising a blast shield coupled to the light guide, the blast shield blocking reflected light from reaching a source of the light energy.

4. The surgical instrument of claim 1, wherein the at least one lens is inside the mounting tube and includes a collimator, a beam-shaping lens distal to the collimator, and a focusing lens distal to the beam-shaping lens.

5. The surgical instrument of claim 4, wherein the beam-shaping lens outputs the light beam substantially in the shape of a line.

6. The surgical instrument of claim 4, wherein the beam-shaping lens includes multiple sub-lenses that provide different beam shapes, wherein the beam-shaping lens is rotatable to select one of the multiple sub-lenses to provide a selected beam shape.

7. The surgical instrument of claim 5, wherein the handle assembly is movable to cause the jaw assembly to exert different pressures on tissue grasped by the jaw assembly.

8. The surgical instrument of claim 1, wherein an entirety of tissue contacting surface of the first jaw member is formed by the window.

9. A surgical method, comprising:
    moving a jaw assembly between an open position and a closed position to grasp tissue, the jaw assembly including:
        a first jaw member non-movably secured to a distal portion of a mounting tube,
        a second jaw member movably secured to the distal portion of the mounting tube, and
        a window secured to the first jaw member and forming a tissue contacting surface, the window being oriented in a plane oblique to a longitudinal axis of the mounting tube,
        wherein the second jaw member is spaced apart from the window when the jaw assembly is in the open position;
    conveying light energy through a light guide to at least one lens positioned distal to the light guide, the light guide being disposed inside the mounting tube and having a distal end ending within the mounting tube, wherein the at least one lens is disposed entirely within the mounting tube;
    focusing the light energy into a light beam using the at least one lens, the light beam provided by the at least one lens entering the jaw assembly; and
    applying the light beam through the window to the tissue grasped by the jaw assembly,
    wherein the window forms a liquid-tight seal between the tissue and the at least one lens.

10. The surgical method of claim 9, further comprising at least one of: reflecting at least a portion of the light beam from a tissue contacting surface of the second jaw member, wherein the tissue contacting surface of the second jaw member includes a light-reflective material, or absorbing at least a portion of the light beam from the tissue contacting surface of the second jaw member, wherein the tissue contacting surface of the second jaw member includes a light-absorbent material.

11. The surgical method of claim 10, further comprising blocking reflected light from reaching a source of the light energy using a blast shield coupled to the light guide.

12. The surgical method of claim 9, wherein focusing the light energy into a light beam using the at least one lens includes:
    collimating the light energy into collimated light energy;
    shaping the collimated light energy into a shaped light energy; and
    focusing the shaped light energy into the light beam.

13. The surgical method of claim 12, wherein the shaped light energy has the shape of a line.

14. The surgical method of claim 12, wherein the at least one lens includes a beam-shaping lens which provides the shaped light energy, the beam-shaping lens including multiple sub-lenses that provide different beam shapes,
    the surgical method further comprising rotating the beam-shaping lens to select one of the multiple sub-lenses to provide a selected beam shape.

15. The surgical method of claim 9, further comprising exerting different pressures on the tissue grasped by the jaw assembly.

16. A surgical system, comprising:
a light energy generator configured to provide light energy; and
a surgical instrument coupled to the light energy generator, the surgical instrument including:
   a mounting tube defining a longitudinal axis and having a proximal portion and a distal portion,
   a light guide disposed inside the mounting tube and configured to convey the light energy, a distal end of the light guide ending within the mounting tube,
   at least one lens positioned entirely inside the mounting tube and distal to the light guide and configured to focus the light energy to provide a light beam,
   a jaw assembly coupled to the distal portion of the mounting tube and positioned distal to the at least one lens such that the light beam provided by the at least one lens enters the jaw assembly, the jaw assembly including:
      a first jaw member non-movably secured to the distal portion of the mounting tube,
      a second jaw member movably secured to the distal portion of the mounting tube, and
      a window secured to the first jaw member and forming a tissue contacting surface, the window being oriented in a plane oblique to the longitudinal axis and forming a liquid-tight seal between tissue and the at least one lens, and
   a handle assembly coupled to the jaw assembly and operable to move the second jaw member between an open position in which the second jaw member is spaced apart from the window and a closed position.

17. The surgical system of claim 16, wherein the second jaw member includes a tissue contacting surface that includes at least one of: a light-reflective material or a light-absorbent material.

18. The surgical system of claim 17, wherein the surgical instrument further includes a blast shield coupled to the light guide, the blast shield blocking reflected light from reaching a source of the light energy.

19. The surgical system of claim 16, wherein the at least one lens is inside the mounting tube and includes a collimator, a beam-shaping lens distal to the collimator, and a focusing lens distal to the beam-shaping lens.

20. The surgical system of claim 19, wherein the beam-shaping lens includes multiple sub-lenses that provide different beam shapes, wherein the beam-shaping lens is rotatable to select one of the multiple sub-lenses to provide a selected beam shape.

\* \* \* \* \*